(12) United States Patent  
Maloney

(10) Patent No.: US 6,481,273 B2
(45) Date of Patent: Nov. 19, 2002

(54) FREQUENCY RESPONSE TEST METHOD FOR AN IN-VEHICLE AIR/FUEL RATIO SENSOR

(75) Inventor: Peter James Maloney, New Hudson, MI (US)

(73) Assignee: Delphi Technologies, Inc., Troy, MI (US)

(*) Notice: Subject to any disclaimer, the term of this patent is extended or adjusted under 35 U.S.C. 154(b) by 87 days.

(21) Appl. No.: 09/782,246

(22) Filed: Feb. 13, 2001

(65) Prior Publication Data

US 2002/0108432 A1 Aug. 15, 2002

(51) Int. Cl.$^7$ ............................................. G01M 15/00
(52) U.S. Cl. ...................................................... 73/118.1
(58) Field of Search ................................ 73/116, 117.2, 73/117.3, 118.1, 119 R

(56) References Cited

U.S. PATENT DOCUMENTS 5,027,646 A * 7/1991 Mizutani et al. ............ 436/160
5,819,195 A * 10/1998 Iwata .......................... 123/672
6,371,096 B1 * 4/2000 Ohsaki et al. ............... 123/688
6,343,499 B1 * 2/2002 Inagaki et al. ............... 123/688

* cited by examiner

Primary Examiner—Eric S. McCall
(74) Attorney, Agent, or Firm—Vincent A. Cichosz

(57) ABSTRACT

An improved method of assessing the frequency response of an in vehicle exhaust gas air/fuel ratio sensor by measuring and analyzing the sensor response to a predetermined perturbation of the fuel delivered to the engine. In a first test mode that provides both quantitative and qualitative assessments, the perturbation is achieved by applying fixed biases to the fuel pulse widths of individual engine cylinders to create a rich/lean perturbation in the exhaust gas, and by adjusting the engine throttle to gradually vary the engine speed over a test interval so that the rich/lean perturbation correspondingly varies in frequency. Since the biases are fixed, intake port wall-wetting effects are minimized. In a second test mode that provides a qualitative assessment, the perturbation is achieved by applying an alternating fuel bias multiplier to every engine cylinder, with the engine operating at a fixed speed and load setting that is of interest for diagnostic purposes. In each case, the output of the air/fuel sensor is band-pass filtered at the frequency of the fuel bias pattern to identify the sensor response, and the response is rectified and low-pass filtered to produce a D.C. measure of the response amplitude to generate a pass/fail indication. In the first test mode, the output of the air/fuel sensor can also be sampled and incrementally processed with a Fast-Fourier-Transform (FFT) technique to identify the response amplitude of the sensor at each of a plurality of frequencies, forming the basis of a Bode plot.

10 Claims, 5 Drawing Sheets

FREQUENCY RESPONSE TEST METHOD FOR AN IN-VEHICLE AIR/FUEL RATIO SENSOR

TECHNICAL FIELD

This invention relates to a diagnostic test method for a motor vehicle air/fuel ratio sensor, and more particularly to a method for in-vehicle frequency response testing.

BACKGROUND OF THE INVENTION

Exhaust gas air/fuel ratio sensors are commonly used for feedback purposes in motor vehicle engine fuel control systems to enable adjustment of engine fuel delivery for achieving a desired intake air/fuel ratio. Consequently, the accuracy of the fuel control under dynamic operating conditions depends to a high degree on the ability of the sensor to quickly respond to changes in the sensed air/fuel ratio. For this reason, it is important to be able to test and verify proper operation of the sensor, both during engine development and periodically during the life of the vehicle.

While formal laboratory testing may be used to determine the frequency response of a sensor, it is impractical to use computationally intensive, formal laboratory analysis methods for field development work and in-use testing. For similar reasons, such analysis methods are also unsuited for on-board diagnostic applications. Accordingly, what is needed is a method of simply and reliably assessing the frequency response of an in-vehicle air/fuel ratio sensor, both for design and development work, and for on-board diagnostic purposes.

SUMMARY OF THE INVENTION

The present invention is directed to an improved method of assessing the frequency response of an in-vehicle exhaust gas air/fuel ratio sensor be measuring and analyzing the sensor response to a predetermined perturbation of the fuel delivered to the engine. A first embodiment best suited for design and development work provides both quantitative and qualitative assessment of the sensor response, and a second embodiment best suited for on-board diagnostics provides a qualitative assessment of the sensor response.

According to the first embodiment, the perturbation is achieved by applying fixed biases to the fuel pulse widths of individual engine cylinders to create a rich/lean perturbation in the exhaust gas, and by adjusting the engine throttle to gradually vary the engine speed over a test interval so that the rich/lean perturbation correspondingly varies in frequency. Since the biases are fixed, intake port wall-wetting effects are minimized. According to the second embodiment, the perturbation is achieved by applying an alternating fuel bias multiplier to every engine cylinder, with the engine operating at a fixed speed and load setting that is of interest for diagnostic purposes.

In both embodiments, the output of the air/fuel sensor is band-pass filtered at the frequency of the fuel bias pattern to identify the sensor response, and the sensor response is rectified and low-pass filtered to produce a D.C. measure of the response amplitude. The D.C. measure is then compared with a threshold response to judge if the frequency response of the sensor is within acceptable limits. In the first embodiment, the output of the air/fuel sensor can also be sampled and incrementally processed with a Fast-Fourier-Transform (FFT) technique to identify the response amplitude of the sensor at each of a plurality of frequencies, forming the basis of a Bode plot characterizing the overall response of the sensor.

DESCRIPTION OF THE PREFERRED EMBODIMENT

Figure 1:
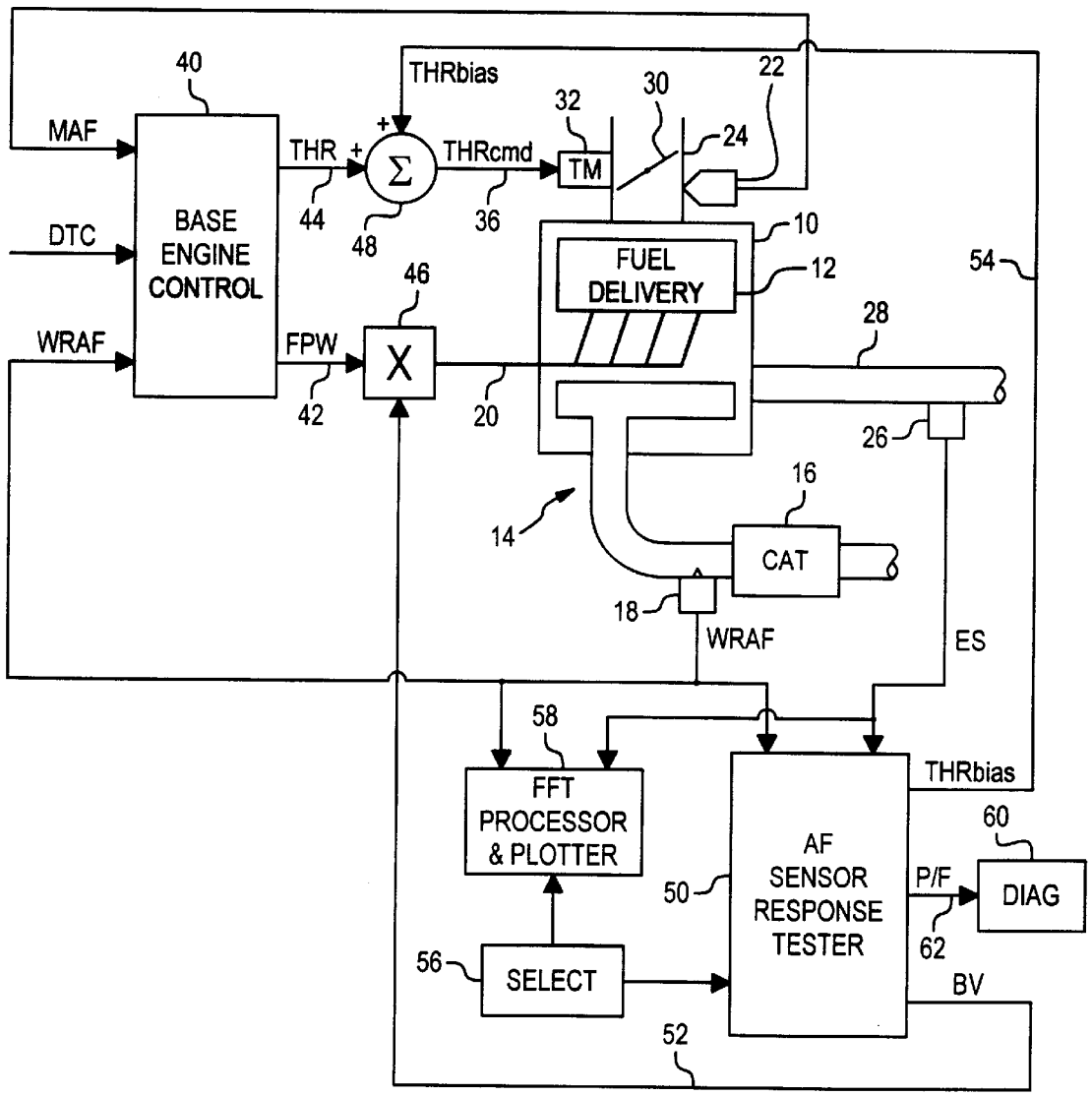
FIG. 1 is a block diagram of an engine fuel delivery system including an exhaust gas air/fuel ratio sensor, and an in-vehicle air/fuel ratio sensor frequency response tester according to this invention.

Referring to FIG. 1, the testing method of this invention is described in the context of a control for a vehicle four-cylinder internal combustion engine 10 having an electronically controlled fuel delivery system 12, and an exhaust system 14 including a three-way catalytic converter 16, and a wide-ratio exhaust gas air/fuel ratio (WRAF) sensor 18 located upstream of catalytic converter 16. The fuel delivery system 12 includes a fuel injector at each engine cylinder, and is activated by an equal number of control lines 20 to enable individual cylinder fuel control. Other sensors depicted in FIG. I include a mass air flow (MAF) sensor 22 coupled to the engine intake manifold 24, and an engine speed (RPM) sensor 26 coupled to the engine output shaft 28. Also in the illustrated embodiment, the engine 10 has a throttle 30 positioned within the manifold 24 by a throttle motor (TM) 32 controlled by a throttle command signal THRcmd on line 36.

The various sensor output signals, including the mass air flow MAF and the air/fuel ratio sensor signal WRAF are applied as inputs, along with a driver torque command signal DTC, to a base engine control block 40. The control block 40, which may be additionally responsive to various other inputs, develops a base fuel pulse width signal FPW on line 42 and a base engine throttle position signal THR on line 44. In a conventional control, the throttle signal THR is applied to line 36 for controlling throttle motor 32, and the base fuel pulse width signal FPW is applied to lines 22 (with or without individual cylinder biases) for controlling the fuel delivery system 12. However, according to this invention, provision is made for perturbation of the fuel pulse width signal (for at least some of the engine cylinders) and adjusting the engine throttle setting for purposes of measuring a frequency response of the air/fuel sensor 18. To this end, a multiplier block 46 is inserted between the fuel pulse width signal FPW on line 42 and the fuel delivery control lines 20, and a summation block 48 is inserted between the base throttle position signal THR on line 44 and the throttle command signal (THRcmd) line 36. Secondary inputs to the multiplier block 46 and summation block 48 are developed by the A/F Sensor Response Tester block 50; specifically, a bias vector BV is applied to multiplier 46 via line 52, and a throttle bias signal THRbias is applied to summation block 48 via line 54. Thus, the throttle command THRcmd is determined according to the sum (THR+THRbias), and the individual cylinder fuel control signals are determined according to the product (FPW * BV).

Figure 2:
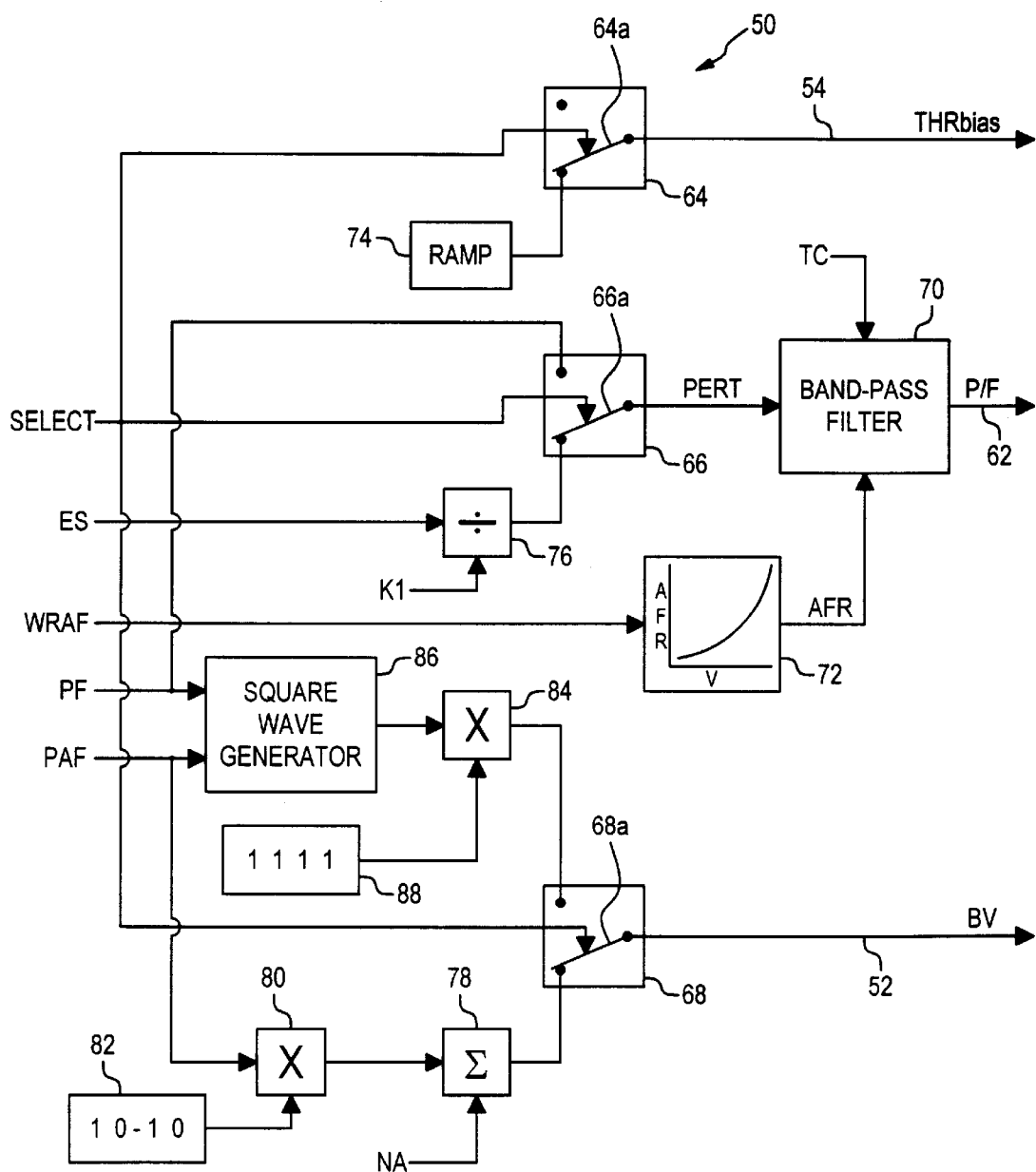
FIG. 2 is a block diagram detailing the air/fuel ratio sensor frequency response tester of FIG. 1.
Figure 3:
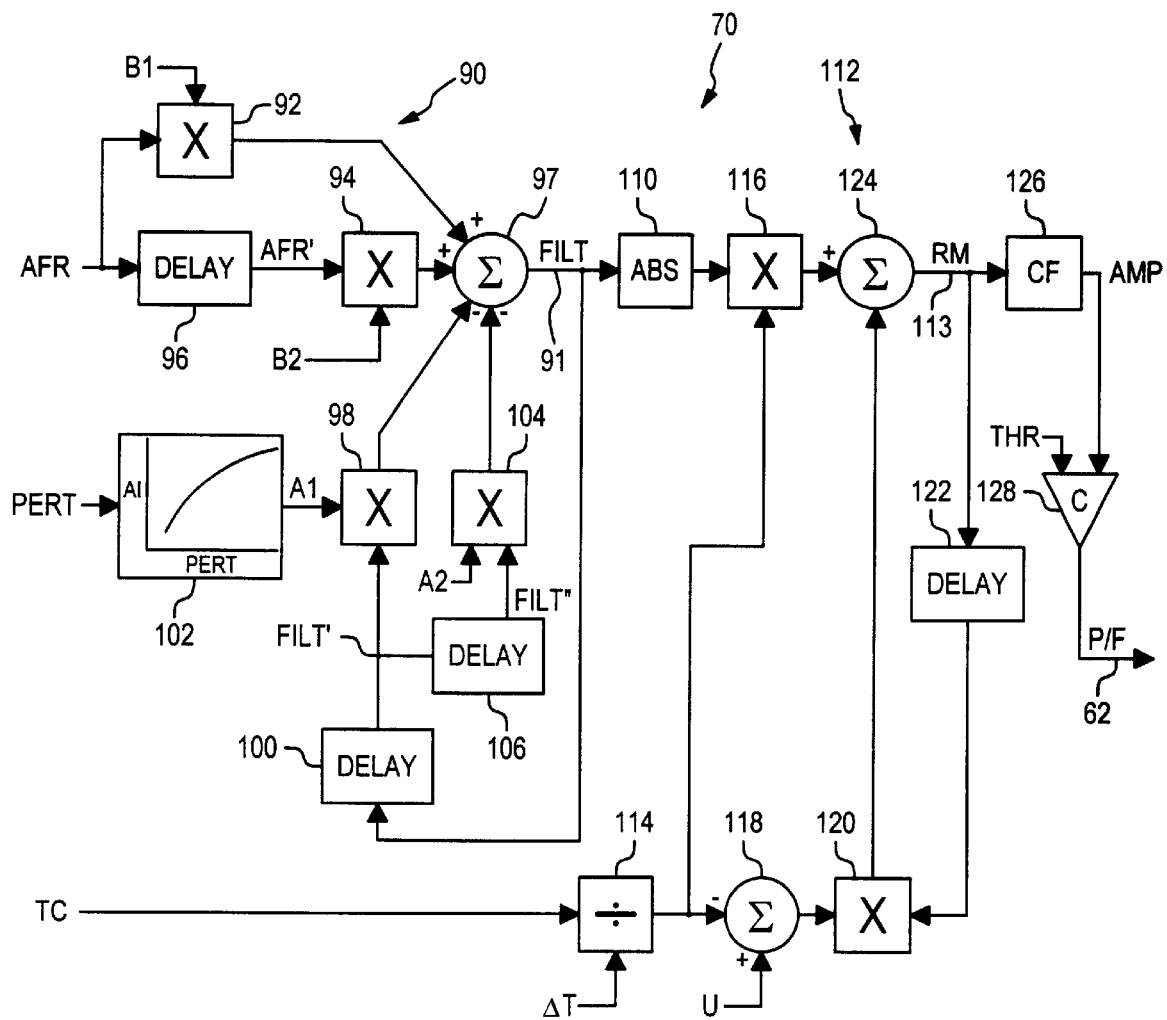
FIG. 3 is a block diagram detailing a band-pass filter generally depicted in FIG. 2.

The A/F Sensor Response Tester block 50 is further described by the block diagrams of FIGS. 2–3, and operates in one of two modes to determine the frequency response of air/fuel ratio sensor 18 by measuring and analyzing the sensor response to a predetermined perturbation of the fuel determined by the bias vector BV. The desired mode is selected by a SELECT input 56, which also supplies an input to block 58, as explained below.

In the first mode, the bias vector BV applies a fixed fuel bias pattern to selected individual engine cylinders to create a rich/lean perturbation in the exhaust gas, and the throttle bias THRbias progressively increases the throttle 30 (and hence, engine speed ES) over a predefined test interval so that the rich/lean perturbation correspondingly varies in frequency. In the second mode, the bias vector BV applies an alternating fuel bias pattern to all of the individual engine cylinders, and the throttle bias THRbias is not used. In either mode, the block 50 band-pass filters the output of the air/fuel sensor 18 at the frequency of the fuel bias pattern to identify the sensor response, and then rectifies and lowpass filters the response to produce a D.C. measure of the response amplitude. The D.C. measure is compared to a threshold; based on the comparison, the block 50 develops a Pass/Fail (P/F) output on line 62 that is applied to a Diagnostic data manager (DIAG) 60 that coordinates on-board diagnostic indications. If the response amplitude exceeds the threshold, the sensor 18 is deemed to pass (P) the test; if the response amplitude fails to exceed the threshold, the sensor is deemed to have failed (F) the test. Additionally, in the first test mode, the block 58 samples the output of the air/fuel sensor 18 during the test interval and incrementally processes the sampled data using a Fast-Fourier-Transform (FFT) technique. This identifies the response amplitude of sensor 18 at each of a plurality of frequencies, forming the basis of a Bode plot characterizing the overall frequency response of sensor 18.

Referring to FIG. 2, the A/F Sensor Response Tester block 50 includes a number of function blocks, including switch blocks 64, 66, 68 and Band-Pass Filter block 70. The switch blocks 64, 66 and 68 are each configured in response to the SELECT input. In a first state, the switch arms 64a, 66a, 68a are deflected downward as shown in FIG. 2 to select the first test mode. In a second state, shown in FIG. 2, the switch arms 64a, 66a, 68a are deflected upward to select the second test mode. And in a third state, the switch arms 64a, 66a, 68a assume an intermediate position for which both test modes are disabled. The Band-Pass Filter 70 is detailed below in reference to the block diagram of FIG. 3, and is tunable based on the fuel perturbation frequency PERT to identify the frequency response of sensor 18 at the perturbation frequency and to produce the Pass/Fail indication P/F on line 62. Since Filter 70 is operable in both test modes, the air/fuel sensor output WRAF is continuously applied as an input to Filter 70. In the illustrated embodiment, a look-up table block 72 converts the sensor output voltage WRAF to an equivalent air/fuel ratio AFR which is applied to Filter 70, but it will be recognized that the sensor output voltage WRAF could be used as the filter input instead of the corresponding air/fuel ratio AFR.

When the first test mode is selected, switch 64 couples the throttle bias THRbias line 54 to Ramp block 74, which develops a saw-tooth waveform having a predetermined ramp rate and frequency for gradually increasing the position of throttle 30 over a given test interval (such as 60 seconds). At the same time, the switch 66 couples the PERT input of filter 70 to divider 76, which determines the perturbation frequency by dividing the engine speed ES by a constant K1. Finally, the switch 68 couples the bias vector (BV) line 52 to the summation block 78, which together with multiplier 80 and vector input 82 produces a bias vector BV that creates a rich/lean perturbation in the exhaust gas. A Perturbation Amplitude Factor PAF calibrates the perturbation amplitude, the multiplier 80 creates a vector output based on PAF and the vector input 82, and the summation block 78 adds a unity magnitude to each component of the vector output. As indicated at block 82, PAF is applied in positive sign to a first engine cylinder and in negative sign to a third cylinder (of the engine firing order), to produce a quasi-sinusoidal perturbation at a frequency that varies with fuel injection frequency, which is directly related to engine speed ES. Preferably, the perturbation amplitude factor PAF is relatively small, and may be calibrated to produce an air/fuel ratio variation (positive and negative) in the range of 0.25 to 0.50, for example. Since the bias has a fixed amplitude, it does not continuously change the fuel pulse width for any given cylinder, and consequently, the effects of fuel wetting on the intake port walls of engine 10 are minimized.

When the second test mode is selected, switch 64 isolates the throttle bias THRbias line 54 from Ramp block 74, the switch 66 couples the PERT input of filter 70 to a calibrated perturbation frequency value PF, and the switch 68 couples the bias vector (BV) line 52 to the multiplier block 84, which together with square-wave generator 86 and vector input 88 produces a bias vector BV that creates an alternating fuel bias pattern in all of the individual engine cylinders based on PF and PAF. The perturbation frequency PF is preferably calibrated within a frequency range (such as 1–8 Hz) that is high enough to prevent engine surging, but below the engine firing frequency under typical test conditions. As indicated above by way of example, the perturbation amplitude factor PAF may be calibrated to produce an air/fuel ratio variation (positive and negative) in the range of 0.25 to 0.50. The square-wave generator 86 is responsive to PF and PAF, and generates a square-wave output have a frequency PF and a magnitude of (1±PAF). The multiplier 84 creates a vector output based on the square-wave and the vector input 88, which applies the square-wave perturbation equally to each of the engine cylinders, as indicated.

If desired, the perturbation frequency PF and perturbation amplitude factor PAF can be varied as a means of enhancing the conversion efficiency of catalytic converter 16. The desired variation may be determined experimentally by adjusting PF and PAF to identify the best catalytic conversion efficiency, and then scheduling PF and PAF accordingly by table look up as a function of specified engine operating conditions, such as exhaust gas flow rate and temperature. In such case, the fueling perturbation is introduced for reasons other than sensor testing, and the testing method is effectively non-intrusive.

Referring to FIG. 3, the filter block 70 includes a Butterworth filter 90 that is tuned based on the input PERT to extract the response of the sensor 18 at the fuel perturbation frequency. The filter output is designated as FILT, and appears on line 91. In the first test mode, the fuel perturbation frequency varies during the test interval, and PERT is computed based on engine speed ES as described above in reference to FIG. 2. In the second test mode, PERT is set to the calibrated or scheduled perturbation frequency value PF. As depicted, the filter output FELT is based on the summation of four terms in summer 97, two of the terms being additive and two being subtractive. A first term is formed by multiplier 92, which forms the product (AFR * B1), where B1 is a fixed coefficient. A second term is formed by multiplier 94, which forms the product (AFR' * B2), where AFR' is the AFR value from the previous filter update (as denoted by the DELAY block 96) and B2 is a fixed coefficient. The third term is formed by multiplier 98, which forms the product (FILT' * A1), where FILT' is the filter output value FILT from the previous filter update (as denoted by the DELAY block 100) and A1 is a coefficient that varies based on PERT. As indicated at block 102, the coefficient A1 may be determined as a function of PERT by table look-up. Finally, the fourth term is formed by multiplier 104, which forms the product (FILT" * A2), where FILT" is the filter output value FILT from two previous filter updates (as denoted by the DELAY blocks 100 and 106) and A2 is a fixed coefficient.

The Butterworth filter output FILT is applied as an input to Absolute Value (ABS) block 110, which provides full-wave rectification, and then to a low-pass filter, generally designated by the reference numeral 112. The low-pass filter 112 is a time-based first-order filter defined by the calibration values ΔT and TC, and develops a response magnitude signal RM on line 113. The term ΔT is the filter update time increment, and TC is the filter time constant. The term U represents a unity offset. The divider 114 divides the update time increment ΔT by TC, and supplies the result to multiplier 116 and summer 118. The summer 118 forms a difference between the output of divider 114 and the offset U, and supplies the result to multiplier 120, which also receives a previous value of the response magnitude RM (i.e., the low-pass filter output) from delay block 122. The multiplier 116 multiplies output of ABS block 110 by the output of divider 114, and the result is summed with the output of multiplier 120 in summer 124 to form the response magnitude signal RM on line 113.

The response magnitude signal RM on line 113 represents the RMS value of the response amplitude. The Conversion Factor (CF) block 126 converts the RMS value to an average amplitude AMP, and the comparator block 128 compares the amplitude AMP to a threshold THR representative of a minimum acceptable response level. If AMP exceeds THR, comparator 128 provides a Pass indication on line 62; otherwise, comparator 128 provides a Fail indication on line 62. The threshold THR may be calibrated as a function of engine operating conditions such as exhaust gas flow, exhaust temperature, exhaust back-pressure, combustion mode, and so forth, to account for the normally occurring characteristics of a good sensor under different operating conditions. Additionally, if the PF and PAF parameters of the second test mode are dynamically varied for converter efficiency enhancement, the threshold THR is adjusted accordingly.

Figure 4:
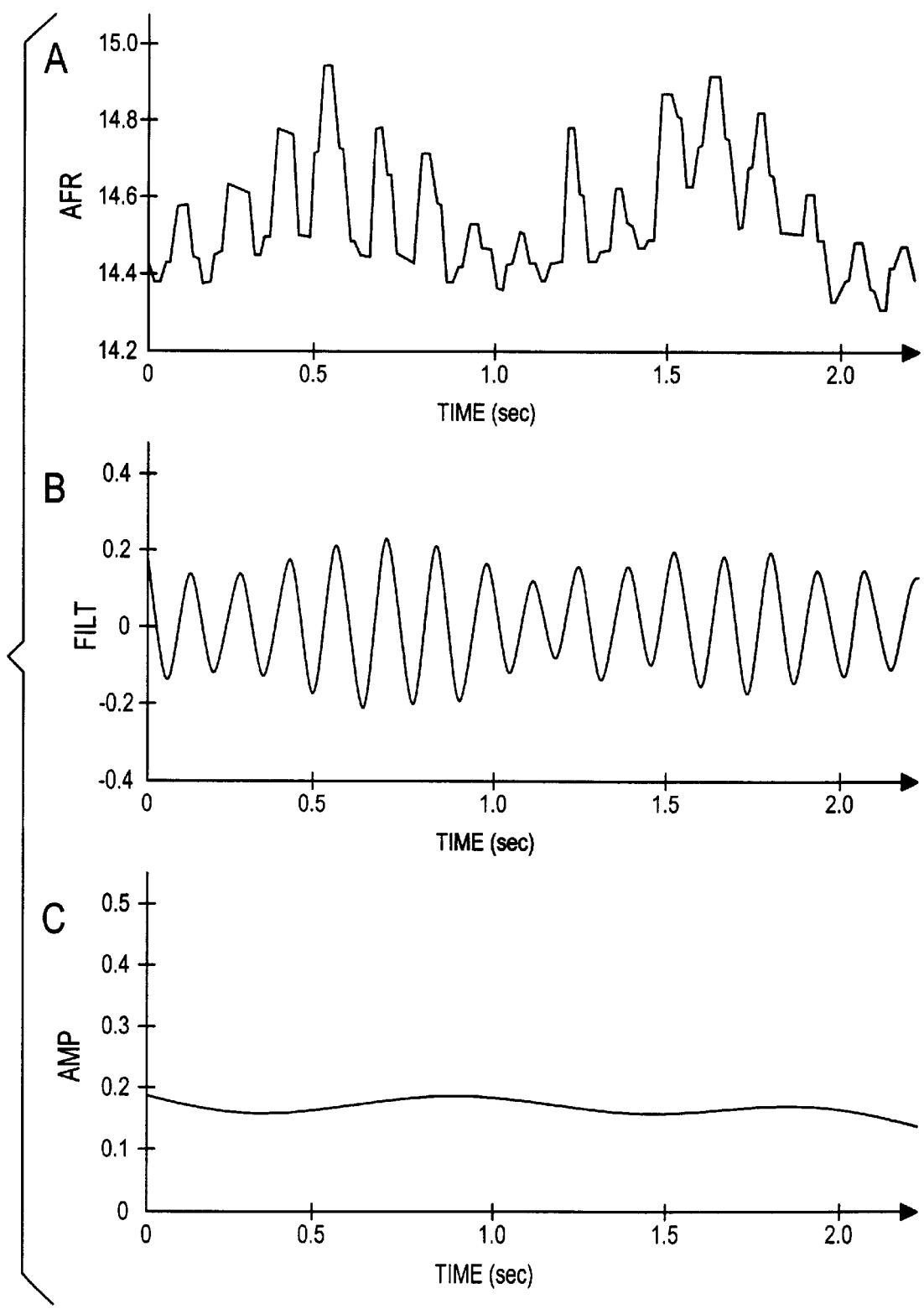
FIG. 4 graphically depicts the operation of the band-pass filter of FIG. 3.

An example of the operation of Filter 70 in response to a perturbation of the engine fueling (by either the first or second test modes) is shown in FIG. 4. Referring to FIG. 4, Graph A depicts a sensed air/fuel ratio AFR, Graph B depicts the output FLT of Butterworth filter 90, and Graph C depicts the amplitude AMP output of Conversion Factor block 126.

Figure 5:
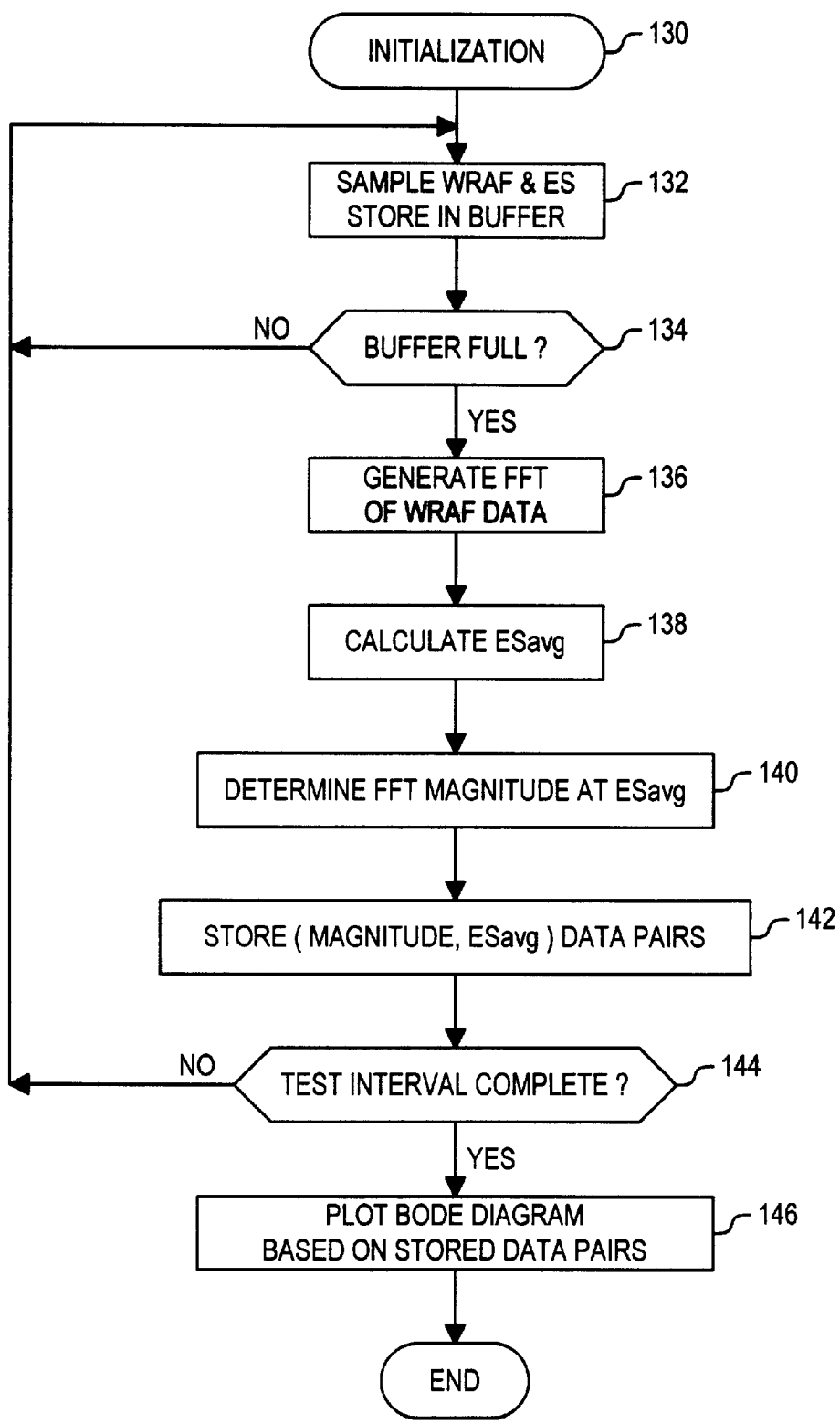
FIG. 5 is a flow diagram illustrating a processing technique employed according to the first embodiment of this invention.

FIG. 5 is a flow diagram representative of the functionality of the block 58 of FIG. 1 when enabled by the SELECT input 56. The block 130 represents a series of instructions for initializing various parameters to known or default states. Following initialization, the block 132 is repeatedly executed to sample the WRAF and ES signals at a predetermined sample rate (such as 1 kHz), and to store the sampled data in a buffer. When the buffer is full, as determined at block 134, the blocks 136, 138, 140 and 142 are executed to perform a Fast-Fourier-Transform (FFT) on the buffered WRAF data, to calculate the average ESavg of the buffered engine speed data, to determine the FFT magnitude at the computed ESavg, and to store the determined (magnitude, ESavg) data pair for the buffered data. As indicated by block 144, the above described blocks 132–142 are then re-executed until the test interval is complete, whereafter block 146 is executed to plot a Bode diagram based on the stored (magnitude, ESavg) data pairs.

In summary, the testing method of this invention provides a practical and cost-effective technique to both qualitatively and quantitatively determine whether an in-vehicle air/fuel ratio sensor such as the WRAF sensor 18 exhibits a sufficiently high frequency response to enable accurate air/fuel ratio control in a vehicle engine. The first test mode is more conducive to off-line testing, and offers a quantitative measure of the frequency response, whereas the second test mode is more conducive to periodic on-board sensor diagnosis, and offers a qualitative pass/fail indication of sensor performance. The qualitative indication is available with either test mode, and can be verified by the quantitative measurements obtained during operation of the first test mode. While the present invention has been described in reference to the illustrated embodiments, it is expected that various modifications in addition to those mentioned above will occur to those skilled in the art. For example, it is unnecessary to design a system capable of selectively performing both test modes. Additionally, the test methods may be used to test either switching or wide-range air/fuel ratio sensors, and so on. Thus, it will be understood that methods incorporating these and other modifications may fall within the scope of this invention, which is defined by the appended claims.

What is claimed is:

1. A method of testing a frequency response of an air/fuel ratio sensor installed in a multi-cylinder internal combustion engine having a fuel system for delivering fuel to individual engine cylinders in accordance with a base fuel pulse command, the method comprising the steps of:

biasing the base fuel pulse command to introduce a perturbation in the fuel delivered to at least one of said engine cylinders during a test interval;

sampling an output of said air/fuel ratio sensor during said test interval;

determining a frequency of said perturbation; and identifying a response of the sampled output at the determined perturbation frequency.

2. The method of claim 1, wherein the step of identifying a response of the sampled output includes the steps of:

band-pass filtering the sampled output at the determined perturbation frequency.

3. The method of claim 2, including the step of:

rectifying and low-pass filtering the band-pass filtered sampled output to determine a magnitude of the identified response.

4. The method of claim 3, including the steps of:

comparing the determined magnitude to a threshold;

providing a pass indication if the determined magnitude exceeds the threshold; and providing a fail indication if the determined magnitude is below the threshold.

5. The method of claim 1, wherein the base fuel pulse command is biased to introduce a perturbation in the fuel delivered to each of said engine cylinders, the perturbation having a predetermined amplitude and alternating above and below said base fuel pulse command at a predetermined frequency.

6. The method of claim 5, wherein the determined frequency of perturbation is said predetermined frequency.

7. The method of claim 1, wherein the base fuel pulse command is biased to introduce a perturbation in the fuel delivered to less than all of said engine cylinders for creating a quasi-sinusoidal perturbation of an air/fuel ratio sensed by said air/fuel ratio sensor.

8. The method of claim 7, including the step of:
progressively adjusting a speed of said engine during said testing interval, thereby to adjust a frequency of said quasi-sinusoidal perturbation.

9. The method of claim 8, wherein the step of determining the frequency of said perturbation includes the steps of:
measuring a speed of the engine; and
determining the frequency of said perturbation based on the measured speed.

10. The method of claim 8, including the steps of:
repeatedly sampling the output of said air/fuel ratio sensor during incremental portions of said test interval; and
for each of said incremental portions:
computing a Fast-Fourier-Transform response of the sampled output;
determining an average speed of said engine; and
identifying a magnitude of the computed Fast-Fourier-Transform response at a perturbation frequency corresponding to the determined average speed.

* * * * *